United States Patent
Kühnle et al.

(10) Patent No.: US 6,852,893 B2
(45) Date of Patent: Feb. 8, 2005

(54) METHOD FOR OXIDIZING HYDROCARBONS

(75) Inventors: Adolf Kühnle, Marl (DE); Mark Duda, Ludwigshafen (DE); Carsten Jost, Marl (DE); Guido Fries, Recklinghausen (DE); Jochen Kirchhoff, Luedinghausen (DE); Thomas Schiffer, Haltern (DE); Roger Arthur Sheldon, VA Rijswijk (NL); Sasidharan Manickam, Tamil Nadu (IN); Isabella W. C. E. Arends, SL'Gravenhage (NL)

(73) Assignee: Creavis Gesellschaft fuer Technologie and Innovation mbH, Marl (DE)

( * ) Notice: Subject to any disclaimer, the term of this patent is extended or adjusted under 35 U.S.C. 154(b) by 0 days.

(21) Appl. No.: 10/239,215

(22) PCT Filed: Mar. 22, 2001

(86) PCT No.: PCT/EP01/03289

§ 371 (c)(1),
(2), (4) Date: Jan. 15, 2003

(87) PCT Pub. No.: WO01/74742

PCT Pub. Date: Oct. 11, 2001

(65) Prior Publication Data

US 2003/0176733 A1 Sep. 18, 2003

(30) Foreign Application Priority Data

Mar. 30, 2000 (DE) .......................... 100 15 880

(51) Int. Cl.[7] .................. C07C 45/00; C07C 309/00; C07C 37/08; C07C 51/16; C07D 235/00
(52) U.S. Cl. .................. 568/314; 568/346; 568/351; 568/385; 568/560; 568/569; 568/768; 562/408; 562/418; 562/497; 562/521; 548/301.4; 548/485
(58) Field of Search .................. 568/314, 346, 568/351, 385, 560, 569, 768; 562/408, 418, 497, 521; 548/301.4, 485

(56) References Cited

U.S. PATENT DOCUMENTS 5,030,739 A    7/1991  Foricher et al. ............ 552/542

FOREIGN PATENT DOCUMENTS

EP          0 885 868        12/1998

OTHER PUBLICATIONS

J. March: "Free–radical substitution" Advanced Organic Chemistry. Reactions, Mechanisms, and Structure, p. 706.

Yasutaka Ishii et al.: "A novel catalysis of n–hydroxyphthalimide in the oxidation of organic substrates by molecular oxygen" Journal of Organic Chemistry, vol. 60, No. 13, pp. 3934–3935, Jun. 30, 1995.

Ishii: "A novel catalysl sof NHPI combined with Co(Acac)n (n=2 or 3) in the oxidation of organic substrates with molecular oxygen" J. Mol. Catal. A, vol. 117, pp. 123–137, 1997.

U.S. Appl. No. 10/239,185, filed Sep. 26, 2002, Kuehnle, et al.

U.S. Appl. No. 10/482,777, filed Jan. 2, 2004, Kuehnle, et al.

*Primary Examiner*—Johann Richter
*Assistant Examiner*—Sikarl A. Witherspoon
(74) *Attorney, Agent, or Firm*—Oblon, Spivak, McClelland, Maier & Neustadt, P.C.

(57) ABSTRACT

The invention relates to a method for oxidizing substrates such as hydrocarbons, waxes or soot. The method involves the use of a compound of formula (I) in which: R1 and R2 represent H, an aliphatic or aromatic alkoxy radical, carboxyl radical, alkoxycarbonyl radical or hydrocarbon radical, each having 1 to 20 hydrocarbon atoms, SO3H, NH2, OH, F, Cl, Br, I and/or NO2, whereby R1 and R2 designate identical or different radicals or R1 and R2 can be linked to one another via a covalent bonding; Q1 and Q2 represent C, CH, N, CR5, each being the same or different; X and Z represent C, S, CH2, each being the same or different; Y represents O and OH; k=0, 1, 2; l=0, 1, 2; m=1 to 3, and; R5 represents one of the meanings of R1. Said compound is used as a catalyst in the presence of a radical initiator, whereby the molar ratio of the catalyst to the hydrocarbon is less than 10 mol %. Peroxy compounds or azo compounds can be used as the radical initiator. Preferred substrates are aliphatic or aromatic hydrocarbons.

19 Claims, No Drawings

METHOD FOR OXIDIZING HYDROCARBONS

The invention relates to a process for catalytically oxidizing substituted or unsubstituted hydrocarbons to the corresponding alcohols, hydroperoxides, carboxylic acids, dicarboxylic acids or ketones.

The oxidation of hydrocarbons is an important reaction in industrial organic chemistry. For these oxidations, compounds such as $KMnO_4$, $CrO_3$ or $HNO_3$ can be used as oxidizing agents. However, firstly, these have the disadvantage of a relatively high price, and secondly their use is accompanied with unwanted coupling products which can represent disposal problems and ecological pollution.

Preferably, therefore, oxidizing agents based on peroxides or $N_2O$ are used. The cheapest oxidizing agent, however, is molecular oxygen, either in pure form or as atmospheric oxygen. Oxygen itself, however, is usually unsuitable for oxidizing hydrocarbons, since the reactivity of the $O_2$ molecule, which occurs in the energetically favorable triplet form, is not sufficient.

By using redox metal catalysts it is possible to utilize molecular oxygen for oxidizing organic compounds. A great number of industrial processes are based on the metal-catalyzed autooxidation of hydrocarbons. Thus, for example, the oxidation cyclohexane with $O_2$ to cyclohexanol or cyclohexanone proceeds with the use of cobalt salts. These industrial processes are based on a free-radical chain mechanism. The bi-radical oxygen reacts with a hydrocarbon free radical, with formation of a peroxy radical and subsequent chain propagation by abstraction of an H atom at a further hydrocarbon. In addition to metal salts, however, organic molecules can also act as free-radical initiators.

It is a disadvantage with these processes that the selectivity decreases very greatly with increasing conversion rate and therefore the processes must be operated at a very low level of conversion rate. Thus, for example, the oxidation of cyclohexane to cyclohexanol/cyclohexanone is carried out at a conversion rate of 10 to 12% so that the selectivity is 80 to 85% ("Industrielle Organische Chemie" [Industrial Organic Chemistry] 1994, 261, VCH-Verlag, D-69451 Weinheim). In a further important industrial autooxidation process, cumene oxidation, the conversion rate is about 30% for a cumene hydroperoxide selectivity of approximately 90% (loc. cit. 385 ff).

An alternative to metal salt catalysts is the use of catalyst systems or mediator systems, for example N-hydroxyphthalimide (NHPI). However, the reaction rate for the processes presented is not satisfactory, despite the high amount of mediator (up to equimolar ratios versus the substrate) (J. Mol. Catalysis A. 1997, 117, 123–137). Thus U.S. Pat. No. 5,030,739 describes the use of N-hydroxydicarboxylic acid imides to oxidize isoprene derivatives to the corresponding acrolein compounds. Although combined oxidation/dehydration of cyclohexadienes or 6-ring systems such as α-terpinene leads to the cumene derivative, this is not further oxidized. This process is therefore unsuitable for converting cumene to cumene hydroperoxide.

In general, amounts of mediator of at least 10 mol % with respect to the substrate are used, with higher amounts of mediator being used to increase the reaction rate (J. Org. Chem. 1995, 60, 3934–3935). The product selectivity is insufficient for industrial use. Thus in the oxidation of cumene with NHPI, a product mixture is obtained containing acetophenone as main product, but the desired oxidation product cumene hydroperoxide was not isolated (J. Org. Chem. 1995, 60, 3934–3935).

A further development of the system is the use of co-catalysts. Co-catalysts which can be used are metal compounds, in particular heavy metal salts, enzymes or strong Brönsted acids. Thus Ishii et al. found that NHPI, in combination with redox metal salts as co-catalyst, can have advantages compared with the analogous oxidation without co-catalyst (for example EP 0878234, EP 0864555, EP 0878458, EP 0858835, JP 11180913, J. Mol. Catalysis A. 1997, 117, 123–137). However, disadvantages of these systems are, in addition to the unwanted heavy metal content, also in this case the high amount of NHPI used. In order to ensure a satisfactory reaction rate, at least 10 mol % of mediator must be used. A further disadvantage is that the redox metals used in part catalyze further reactions of the products and thus decrease the selectivity of the reaction.

Oxidation products of saturated cyclic hydrocarbons, for example cyclopentadecanone, cyclododecanone or cyclooctanone are important odor compounds or odor compound precursors. High purity requirements are made of these substances, so that even metal salts present in catalytic amounts pose great problems. Required workup steps, for example removing the metal compounds, and in particular recovering the added metal salts reduce the efficiency of a metal-salt-catalyzed process and pollute the environment.

Processes have also become known which use only a mediator without co-catalyst. However, these are limited to oxidizing particularly activated substrates, such as ethers, esters or isoprene derivatives.

Thus in the oxidization of cumene using the system NHPI/cobalt acetate, a product mixture of acetophenone (selectivity 54%), 2-phenyl-2-propanol (10%) and phenol (17%) is obtained. The wanted product cumene hydroperoxide is only formed as an intermediate and is not stable under the given process conditions.

A further process variant is the use of NHPI together with alcohols or aldehydes as co-catalyst (Chem. Commun. 1999, 727–728, Tetrahedron Letters 1999, 40, 2165–2168, Chem. Commun. 1997, 447–448). Disadvantages of these processes are the formation of coupling products and the high mediator/substrate ratio used (10 mol %).

DE 19723890 describes an oxidation system consisting of an organic mediator and the redox enzyme laccase for preparing aromatic and heteroaromatic aldehydes and ketones. Here also, the amount of mediator used is very high. In addition, this process, due to the use of an enzyme, has a complicated reaction system using a biologically necessary buffer system, which restricts the broad applicability of this system.

It was an object of the present invention to develop a heavy-metal-free or metal-free process for oxidizing hydrocarbons which has high selectivities with high conversion rates.

Surprisingly, it has been found that compounds of the type

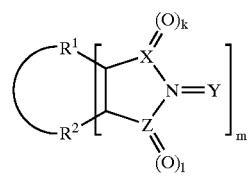

or derivatives of these compounds can be used for oxidizing substrates such as hydrocarbons even without heavy metals or strong acids.

The present invention therefore relates to a process of catalytically oxidizing saturated or unsaturated substituted or unsubstituted hydrocarbons, hetero-cycles, alcohols, ethers, ketones, aldehydes, amines or soot (hereinafter: the substrate) to the corresponding hydroperoxide, alcohol, ketone, carboxylic acid or dicarboxylic acid, in which the catalyst used is a compound of the formula I

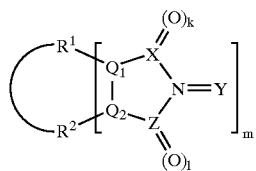

where
R$^1$, R$^2$=H, aliphatic or aromatic alkoxy radical, carboxyl radical, alkoxycarbonyl radical or hydrocarbon radical, each of which has 1 to 20 carbon atoms, SO$_3$H, NH$_2$, OH, F, Cl, Br, I and/or NO$_2$ where R$^1$ and R$^2$ are identical or different radicals, or R$^1$ and R$^2$ can be linked to one another via a covalent bond
Q$_1$, Q$_2$=C, CH, N, CR$^5$, identical or different in each case
X, Z=C, S, CH$_2$, identical or different in each case
Y=O, OH
k=0, 1, 2
l=0, 1, 2
m=1 to 3;
R$^5$: one of the meanings of R$^1$
is used in the presence of a free-radical initiator, the molar ratio of the catalyst to the hydrocarbon being less than 10 mol %.

In the inventive process, no metal compounds or enzymes are used as co-catalyst. The process is preferably carried out in organic solvents in the absence of strong acids; the use of an aqueous solution in the neutral to basic pH range is also possible.

The molar ratio of the catalyst to the hydrocarbon to be oxidized can be between 10$^{-6}$ mol % and 10 mol %, preferably between 10$^{-6}$ and 5 mol %, very particularly preferably between 10$^{-6}$ and 2.5 mol %, and in a special embodiment between 10$^{-6}$ and 1 mol %.

The use of the catalyst (mediator) according to formula I in this low ratio to the substrate to be oxidized, surprisingly, not only achieves high conversion rates at short reaction times, but is also characterized by the achieved selectivities compared with the prior art. A further advantage of the inventive process is improving the economic efficiency by reducing the amount of mediator.

In special embodiments of the inventive process, derivatives or special cases of compounds of the formula I can also be used.

Preference is given to mediators/catalysts of the formula II, that is to say compounds according to formula I where m=1.

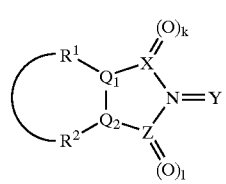

Q$^1$, Q$^2$, R$^1$, R$^2$, X, Y, Z, k and l have the meanings defined for formula I.

Particular preference is given to mediators/catalysts of the formula III

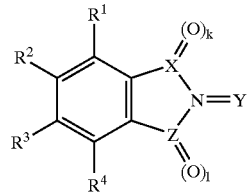

where
R$^1$, R$^2$, R$^3$, R$^4$=H, aliphatic or aromatic alkoxy radical, carboxyl radical, alkoxycarbonyl radical or hydrocarbon radical, each of which has 1 to 20 carbon atoms, SO$_3$H, NH$_2$, OH, F, Cl, Br, I and/or NO$_2$ where R$^1$, R$^2$, R$^3$ and R$^4$ can be identical or different radicals, where
X, Z=C, S, CH$_2$ are identical or different in each case
Y=O, OH
k=0, 1, 2
l=0, 1, 2.

Furthermore, in the inventive process, a hydantoin derivative of the formula IX

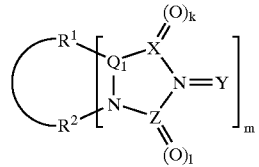

can be used,
where Q$^1$, R$^1$, R$^2$, X, Z, k, l, m have the meanings specified in claim 1.

Examples of the catalysts according to formula I used in the inventive process are N-hyroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-Hydroxybenzene-1,2,4-tricarboximide, N,N'-dihydroxypyromellitimide, N,N'-dihydroxybenzophenone-3,3',4,4'tetracarboximide, N-hydroxymaleimide, pyridine-2,3-dicarboximide, N-hydroxysuccinimide, N-hydroxytartarimide, N-hydroxy-5-norbonene-2,3-dicarboximide, exo-N-hydroxy-7-oxa-bicyclo[2.2.1]hept-5-ene-2,3-dicarboximide, N-hydroxy-cis-cyclohexane-1,2-dicarboximide, N-hydroxy-cis-4-cyclohexene-1,2-dicarboximide, N-hydroxynaphthalimide sodium salt, hydantoin, hydantoin derivatives or N-hydroxy-o-benzenedisulfonimides.

In a particular embodiment of the invention the oxidation is carried out in the liquid phase at a temperature of 0 to 500° C., preferably 50 to 300° C., particularly preferably at a temperature of 50 to 200° C. In this case not only can a solvent or solvent mixture be used, but also the substrate itself can be used as solvent.

The substrates to be oxidized generally belong to the group of substituted or unsubstituted saturated or unsaturated hydrocarbons. Using the inventive process, a multiplicity of these compounds, such as aromatics, aliphatics, olefins or alicyclics, can be selectively oxidized. The substrates for the process of the invention can contain oxygen, sulfur and/or nitrogen atoms and/or cyano groups. In particular, the process according to the present invention can be used for oxidizing cyclic and noncyclic alkanes, alkenes, alcohols, aldehydes, ketones, amines, nitrogen heterocycles, organic sulfides and sulfoxides, cyano-containing compounds, benzene, toluene derivatives and alkylaromatics. Examples of such compounds are, in particular, ethane, ethene, ethyne, propyne, aminocyclododecane, butadiene, butene, butylbenzene, cumene, cyclodecanol, cyclodecane, cyclodecene, cyclododecadiene, cyclododecane, cyclododecanol, cyclohexane, cyclohexanol, cyclohexene, cyclohexanone, cyclododecanone, cyclododecatriene, cyclododecene, cyclododecylbenzene, cycloheptene, cyclohexylbenzene, cyclononene, cyclooctadiene, cyclooctane, cyclooctanol, cyclooctanone, cyclooctene, cyclopentadecane, cyclopentadecanol, cyclopentadecanone, cyclopentadecatriene, cyclopentadecene, cyclopentadecadiene, decalin, dicyclododecyl ether, ethylbenzene, isobutane, isobutene, isophorone, isophorone derivatives, meta-xylene, ortho-xylene, para-xylene, picoline, propane, propene, tetralin, toluene, trimethylcyclohexane, trimethylcyclohexanol, trimethylcyclohexanone, trivinylcyclohexane, in each case as pure substance, in solution or as a mixture.

In the oxidation of cyclic compounds, ring cleavage can occur with formation of dicarboxylic acids, ketones, aldehydes and alcohols.

It is also possible to use the inventive process for freeing waste waters from these compounds by oxidation.

Using this process, the oxidation of waxes of natural and synthetic origin, in particular hydrocarbon waxes, such as paraffins, microwaxes, polyethylene waxes and polypropylene waxes and Fischer-Tropsch waxes, can also be carried out efficiently. Also, what is termed ammoxidation, where a substrate is oxidized in the presence of ammonia, and as a result nitriles are prepared, is also possible using the present process.

In the content of the present invention, soots, which contain a carbon skeleton having a certain proportion of incorporated hydrocarbons, are to be considered hydrocarbons. Oxidative surface treatment of soots which, for example, are used as fillers and/or for coloring polymers or rubbers, is also a potential use of the inventive process. In the case of surface oxidation of soots, not only the purely oxidative surface treatment, but also ammoxidation, is of great industrial interest.

In principle, using the inventive process, by targeted oxidation of carbon atoms or heteroatoms, alcohols, aldehydes, ketones, carboxylic acids, dicarboxylic acids, in particular α-ω-dicarboxylic acids, epoxides, N oxides, sulfoxides, sulfones and sulfonic acids can be prepared.

Preferably, a hydrocarbon having a primary, secondary or tertiary carbon atom can be oxidized to the corresponding hydroperoxide. The oxidation is therefore carried out at a CH bond. Quaternary carbon atoms which only have C—C bonds are not oxidized by the inventive process, but cleaved. Preferably, the substrates used are hydrocarbons having a secondary or tertiary carbon atom, particularly preferably compounds having a tertiary carbon atom of the formula

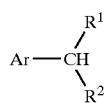

IV where $R^1$, $R^2$=H, aliphatic or aromatic hydrocarbon radical having 1 to 20 carbon atoms, where $R^1$ and $R^2$ are identical or different radicals and $R^1$ and $R^2$ can be linked to one another via a covalent bond and Ar=aromatic hydrocarbon radical.

Examples of compounds of the formula IV are cumene, cyclohexylbenzene, cyclododecylbenzene, ethylbenzene and 2-n-butylbenzene.

Further preferred substrates of the inventive process are compounds of the formulae V, VI, VII and VIII, where Ar is an aromatic hydrocarbon radical.

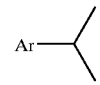

V

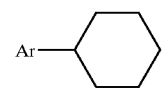

VI

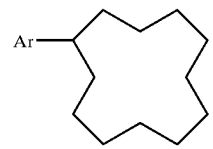

VII

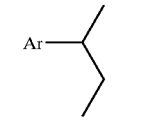

VIII

Oxidizing these hydrocarbons according to the process of the invention leads to the corresponding hydroperoxides, alcohols, aldehydes, ketones or caboxylic acids.

The aromatic hydrocarbon radical Ar in the formulae IV to VIII is a phenyl radical, naphthyl radical or diphenyl radical.

Furthermore, the substrate to be oxidized can be a cyclic, saturated, substituted or unsubstituted hydrocarbon of the formula X

X where n=3 to 21.

Furthermore, the substrate to be oxidized can be a cyclic, saturated, substituted or unsubstituted hydrocarbon of the formula XI

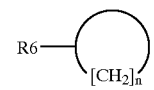

XI where $R^6$=OH or an alkyl chain having 1–10 carbon atoms and n=3–21.

The inventive reaction can proceed in the gas phase, in the liquid phase or in the solid phase. The gas phase as a reaction medium is industrially relevant when readily volatile substances such as propane, propene, butane, butene, isobutane and isobutene, for example, are to be oxidized to the corresponding aldehydes or carboxylic acids. The solid phase comes into consideration in the surface modification of solid products, such as soots. In this case, for example, heated fluidized-bed baths or rotary kilns are used. However, particular preference is given to oxidation in the liquid phase. The substrate to be oxidized can also itself serve as solvent.

The inventive process is presumed to form first the corresponding hydroperoxides. These can, depending on stability, be isolated and specifically further processed, or further reaction (that is to say elimination or rearrangement of the hydroperoxide) proceeds in situ under the chosen reaction conditions to give the secondary products (aldehydes, ketones or mono- or dicarboxylic acids).

The reaction mixture contains a free-radical initiator which decomposes with the formation of free radicals, that is to say the free-radical initiating molecules, such as a peroxy compound or an azo compound. Examples of such compounds are cumene hydroperoxide, cyclohexylbenzene hydroperoxide, cyclododecylbenzene hydroperoxide, 1,4-di(2-neodecanoylperoxyisopropyl)benzene, acetylcyclohexanesulfonyl peroxide, cumyl peroxyneodecanoate, dicyclohexyl peroxydicarbonate, di(4-tert-butylcyclohexyl) peroxydicarbonate, di(2-ethylhexyl) peroxydicarbonate, dimyristyl peroxydicarbonate, dicetyl peroxydicarbonate, tert-butyl peroxyneodecanoate, tert-amyl peroxyneodecanoate, tert-amyl peroxypivalate, tert-butyl peroxypivalate, diisononanoyl peroxide, didecanoyl peroxide, tert-butyl peroxy-2-ethylhexanoate, tert-butyl peroxyisononanoate, 2,2'-di-tert-butylperoxybutane, di-tert-butyl peroxybenzoate, di-tert-butyl peroxide, tert-butyl hydroperoxide, 3,4-dimethyl-3,4-diphenylhexane, dibenzoyl peroxide, 1,4-di-tert-butylperoxycyclohexane, tert-butyl peroxyethylhexylcarbonate, 1,1-di-tert-butylperoxycyclohexane, 2,2'-azobis(2,4-dimethylvaleronitrile, 2,2'-azobis(2-methyl-propionitrile), 1,1'-azobis(cyclohexanecarbonitrile) or cyclohexylhydroperoxide. Obviously, peroxides and azocompounds formed as intermediates can also be used as free-radical initiators.

Preference is given to a free-radical initiator which contains an oxygen atom bound to a secondary or tertiary carbon atom, particular preference is given to a free-radical initiator which is derived from the end product and contains at least one oxygen atom bound to a primary, secondary or tertiary carbon atom. The free-radical initiator is either added separately or as mentioned above generated as an intermediate during the reaction or it is even still present in small amounts from preceding reactions, since a production plant cannot be purified absolutely. Examples of such compounds are cumene hydroperoxide (1-methyl-1-phenylethyl hydroperoxide), cyclohexylbenzene hydroperoxide (1-phenylcyclohexylhydroperoxide), cyclododecylbenzene hydroperoxide (1-phenylcyclododecyl hydroperoxide) and 2-n-butylbenzene hydroperoxide (1-methyl-1-phenylpropyl hydroperoxide).

The concentration of the free-radical initiating molecule (for example hydroxyl radical) in the inventive process at the start of the reaction is frequently less than the concentration of the catalyst. It must be noted, however, that in the course of the reaction these compounds are formed as intermediates, so that the concentration of the free-radical initiating molecules increases in the course of the reaction.

The molar ratio of free-radical initiator to the catalyst can be 4:1, preferably 3:1, very particularly preferably 2:1, or still less, such as 1:1 to 0.5:1. The concentration of the free-radical initiating molecule is dependent on the reaction parameters such as temperature or reaction time.

The lower the content of the free-radical initiator, the slower becomes the reaction, since a certain content of free-radical initiating molecules must first be formed. The amount of free-radical initiator can be reduced still further at the cost of selectivity, if higher temperatures are employed.

The oxidation product formed can be isolated as such, but a direct further reaction of this compound to form a further product is also possible. It is possible to isolate the product by any customary industrial process, for example distillation or crystallization.

The inventive process can be carried out not only batchwise, in the fed-batch procedure, but also continuously.

The inventive process can be carried out using an oxygen-containing gas as oxidizing agent. The proportion of oxygen in the gas can be from 5 to 100% by volume. Preferably, atmospheric oxygen or pure oxygen is used as oxidizing agent. In this case intimate mixture of the liquid and gaseous phases must be ensured. This can be achieved, for example, in stirred tanks by an appropriate stirrer speed or by internals, and in tubular reactors by packing elements and also with bubble columns.

The inventive process can be carried out not only at slightly reduced pressure, but also at atmospheric pressure and also at elevated pressure up to 100 bar. Preference is given to a pressure of 1 bar to 50 bar, particular preference is given to a pressure of 1 bar to 20 bar.

The examples below are intended to describe the invention in more detail but without limiting its scope.

The conversion rate of the reaction was determined firstly by titration of the hydroperoxide with iodine and secondly by GC analysis using an internal standard (naphthalene). The selectivity of the reaction was also determined by GC analysis using an internal standard (likewise naphthalene).

EXAMPLE 1

(ACCORDING TO THE INVENTION)

0.3 mmol of N-hydroxyphthalimide and 0.6 mmol of 1-cyclohexylbenzyl hydroperoxide are added at a temperature of 110° C. to 30 mmol of cyclohexylbenzene in a round-bottomed flask having an attached reflux condenser. The reaction mixture is stirred for 8 hours at said temperature under an oxygen atmosphere of 1 bar. 1-cyclohexylbenzene hydroperoxide is obtained at a selectivity of 96.2% at a cyclohexylbenzene conversion rate of 28.6%.

EXAMPLE 2

(NOT ACCORDING TO THE INVENTION, WITH CO-CATALYST)

0.3 mmol of N-hydroxyphthalimide and 0.3 mmol of Co(II) acetate are added at a temperature of 110° C. to 30 mmol of cyclohexylbenzene in a round-bottomed flask with an attached reflux condenser. The reaction mixture is stirred for 8 hours at said temperature under an oxygen atmosphere of 1 bar. 1-cyclohexylbenzene hydroperoxide is obtained at a selectivity of 54.1% at a cyclohexylbenzene conversion rate of 18.7%.

EXAMPLE 3

(ACCORDING TO THE INVENTION)

0.3 mmol of N-hydroxyphthalimide and 0.6 mmol of cumene hydroperoxide are added at a temperature of 125° C. to 30 mmol of cumene in a round-bottomed flask having an attached reflux condenser. The reaction mixture is stirred for 8 hours at said temperature under an oxygen atmosphere of 1 bar. Cumene hydroperoxide is obtained at a selectivity of 99.9% at a cumene conversion rate of 30.8%.

EXAMPLE 4

(NOT ACCORDING TO THE INVENTION, WITH CO-CATALYST)

0.3 mmol of N-hydroxyphthalimide and 0.3 mmol of Co(II) acetate are added at a temperature of 125° C. to 30 mmol of cumene in a round-bottomed flask having an attached reflux condenser. The reaction mixture is stirred for 8 hours at said temperature under an oxygen atmosphere of 1 bar. Not the target product, but acetophenone is obtained at a selectivity of 58.7%, 2-phenyl-2-propanol (13.1%) and phenol (10.4%) at a cumene conversion rate of 49.3%.

EXAMPLE 5

(ACCORDING TO THE INVENTION)

0.3 mmol of N-hydroxyphthalimide and 0.6 mmol of cyclododecylbenzene hydroperoxide are added at a temperature of 125° C. to 30 mmol of cyclododecylbenzene in a round-bottomed flask having an attached reflux condenser. The reaction mixture is stirred for 8 hours at said temperature under an oxygen atmosphere of 1 bar. Cyclododecylbenzene hydroperoxide is obtained at a selectivity of 95.1% at a cyclododecylbenzene conversion rate of 23.1%.

EXAMPLE 6

(NOT ACCORDING TO THE INVENTION, WITH CO-CATALYST)

0.03 mmol of N-hydroxyphthalimide and 0.03 mmol of Co(II) acetate are added at a temperature of 125° C. to 30 mmol of cyclododecylbenzene in a round-bottomed flask having an attached reflux condenser. The reaction mixture is stirred for 8 hours at said temperature under an oxygen atmosphere of 1 bar. Cyclododecylbenzene hydroperoxide is obtained at a selectivity of 59.1% at a cyclododecylbenzene conversion rate of 7.3%.

EXAMPLE 7

(ACCORDING TO THE INVENTION)

0.3 mmol of N-hydroxyphthalimide and 0.6 mmol of ethylbenzene hydroperoxide are added at a temperature of 125° C. to 30 mmol of ethylbenzene in a round-bottomed flask having an attached reflux condenser. The reaction mixture is stirred for 8 hours at said temperature under an oxygen atmosphere of 1 bar. Ethylbenzene hydroperoxide is obtained at a selectivity of 99.9% at an ethylbenzene conversion rate of 8%.

EXAMPLE 8

(NOT ACCORDING TO THE INVENTION, WITH CO-CATALYST)

0.3 mmol of N-hydroxyphthalimide and 0.3 mmol of Co(II) acetate are added at a temperature of 125° C. to 30 mmol of ethylbenzene in a round-bottomed flask having an attached reflux condenser. The reaction mixture is stirred for 8 hours at said temperature under an oxygen atmosphere of 1 bar. Ethylbenzene hydroperoxide is obtained at a selectivity of 22.4% at an ethylbenzene conversion rate of 0.5%.

EXAMPLE 9

(ACCORDING TO THE INVENTION)

0.3 mmol of N-hydroxyphthalimide and 0.6 mmol of cumene hydroperoxide are added at a temperature of 125° C. to 30 mmol of toluene in a round-bottomed flask having an attached reflux condenser. The reaction mixture is stirred for 8 hours at said temperature under an oxygen atmosphere of 1 bar. Benzyl hydroperoxide is obtained at a selectivity of 51.7% at a toluene conversion rate of 8%. Other products are benzaldehyde (24.6%) and benzoic acid (23.6%).

EXAMPLE 10

(NOT ACCORDING TO THE INVENTION, WITH CO-CATALYST)

0.3 mmol of N-hydroxyphthalimide and 0.3 mmol of Co(II) acetate are added at a temperature of 125° C. to 30 mmol of toluene in a round-bottomed flask having an attached reflux condenser. The reaction mixture is stirred for 8 hours at said temperature under an oxygen atmosphere of 1 bar. Benzyl hydroperoxide is obtained at a selectivity of 18.9% at a toluene conversion rate of 3.7%. In addition there is a multitude of other products, including benzaldehyde and benzoic acid.

EXAMPLE 11

(ACCORDING TO THE INVENTION)

In a 2 l glass vessel having an internal glass frit (for air introduction), 500 g of a polyethylene wax having an osmometric molecular weight of 1450 and an acid value of 0 mg of KOH/g of wax were oxidized at 170° C. with air (flow rate 6 l/min), with addition of 0.1 g of N-hydroxyphthalimide in the melt. After 3 hours an acid value of 23 mg of KOH/g of wax was achieved. The product retained its characteristic white color.

EXAMPLE 12

(NOT ACCORDING TO THE INVENTION, WITH CO-CATALYST)

In a 2 l glass vessel having an internal glass frit (for air introduction), 500 g of a polyethylene wax having an osmometric molecular weight of 1450 and an acid value of 0 mg of KOH/g of wax were oxidized at 170° C. with air (flow rate 6 l/min), with addition of 0.1 g of N-hydroxyphthalimide and 0.22 g of Co(II) acetate in the melt. Not until after 6 hours was an acid value of 17 mg of KOH/g of wax achieved. The product was yellowish-brown.

EXAMPLE 13

(ACCORDING TO THE INVENTION)

2 mmol of N-hydroxyphthalimide and 4 mmol of cumene hydroperoxide are added at a temperature of 130° C. to 200 mmol of cyclopentadecane in a round-bottomed flask having an attached reflux condenser. Oxygen at approximately 15 l/h is passed through the reaction mixture for 8 hours at said temperature. Cyclopentadecanol is obtained at a selectivity of 20% and cyclopentadecanone at a selectivity of 46%, at a cyclopentadecane conversion rate of 44%.

EXAMPLE 14

(ACCORDING TO THE INVENTION)

2 mmol of N-hydroxyphthalimide and 4 mmol of cumene hydroperoxide are added at a temperature of 130° C. to 200 mmol of cyclopentadecane in a round-bottomed flask having an attached reflux condenser. Air is passed at approximately 15 l/h through the reaction mixture for 8 hours at said temperature. Cyclopentadecanol is obtained at a selectivity of 19% and cyclopentadecanone at a selectivity of 48%, at a cyclopentadecane conversion rate of 46%.

EXAMPLE 16

(ACCORDING TO THE INVENTION)

2 mmol of N-hydroxyphthalimide and 4 mmol of cumene hydroperoxide are added at a temperature of 130° C. to 200 mmol of cyclooctane in a round-bottomed flask having an attached reflux condenser. Oxygen at approximately 15 l/h is passed through the reaction mixture for 8 hours at said temperature. Cyclooctanol is obtained at a selectivity of 17% and cyclooctanone at a selectivity of 46%, at a cyclooctcane conversion rate of 53%.

EXAMPLE 17

(ACCORDING TO THE INVENTION)

2 mmol of N-hydroxyphthalimide and 4 mmol of di-tert-butyl peroxide are added at a temperature of 130° C. to 200 mmol of cyclooctane in a round-bottomed flask having an attached reflux condenser. Air at approximately 15 l/h is passed through the reaction mixture for 8 hours at said temperature. Cyclooctanol is obtained at a selectivity of 15% and cyclooctanone at a selectivity of 43%, at a cyclooctane conversion rate of 51%.

EXAMPLE 18

(ACCORDING TO THE INVENTION)

2 mmol of N-hydroxyphthalimide and 4 mmol of cumene hydroperoxide are added at a temperature of 130° C. to 200 mmol of cyclododecane in a round-bottomed flask having an attached reflux condenser. Oxygen at approximately 15 l/h is passed through the reaction mixture for 8 hours at said temperature. Cyclododecanol is obtained at a selectivity of 17% and cyclododecanone at a selectivity of 43%, at a cyclododecane conversion rate of 49%.

EXAMPLE 19

(ACCORDING TO THE INVENTION)

2 mmol of N-hydroxyphthalimide and 4 mmol of cumene hydroperoxide are added at a temperature of 130° C. to 200 mmol of cyclododecane in a round-bottomed flask having an attached reflux condenser. Air at approximately 15 l/h is passed through the reaction mixture for 8 hours at said temperature. Cyclododecanol is obtained at a selectivity of 18% and cyclododecanone at a selectivity of 42%, at a cyclododecane conversion rate of 47%.

What is claimed is:

1. A process for catalytically oxidizing saturated or unsaturated substituted or unsubstituted hydrocarbons, heterocycles, alcohols, ethers, ketones, aldehydes, amines or soot (substrate) to the corresponding hydroperoxide, alcohol, ketone, carboxylic acid or dicarboxylic acid, wherein the catalyst used is a compound of the formula I

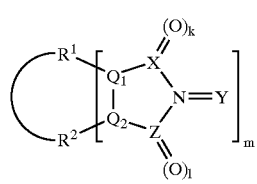

I where $R^1$, $R^2$=H, aliphatic or aromatic alkoxy radical, carboxyl radical, alkoxy-carbonyl radical or hydrocarbon radical, each of which has 1 to 20 carbon atoms, $SO_3H$, $NH_2$, OH, F, Cl, Br, I and/or $NO_2$ where $R^1$ and $R^2$ are identical or different radicals, or $R^1$ and $R^2$ can be linked to one another via a covalent bond $Q_1$, $Q_2$=C, CH, N, $CR^5$, identical or different in each case X, Z=C, S, $CH_2$, identical or different in each case

Y=O, OH k=0, 1, 2 l=0, 1, 2 m=1 to 3;

$R^5$: one of the meanings of $R^1$ is used in the presence of a free-radical initiator, the molar ratio of the catalyst to the hydrocarbon being between $10^{-6}$ mol % and 2.5 mol %.

2. The process as claimed in claim 1, wherein the catalyst used is a compound of the formula III

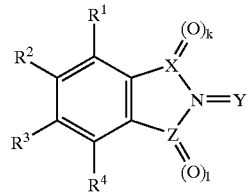

III where $R^1$, $R^2$, $R^3$, $R^4$=H, aliphatic or aromatic alkoxy radical, carboxyl radical, alkoxy-carbonyl radical or hydrocarbon radical, each of which has 1 to 20 carbon atoms, $SO_3H$, $NH_2$, OH, F, Cl, Br, I and/or $NO_2$ where $R^1$, $R^2$, $R^3$ and $R^4$ can be identical or different radicals, where X, Z=C, S, $CH_2$ are identical or different in each case

Y=O, OH k=0, 1, 2 l=0, 1, 2.

3. The process as claimed in claim 1, wherein the catalyst used is a hydantoin derivative of the formula IX

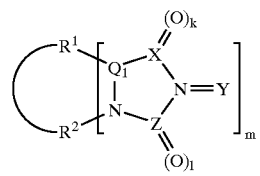

IX where $Q^1$, $R^1$, $R^2$, X, Z, k, l, m have the meanings specified in claim 1.

4. The process as claimed in claim 1, wherein the free-radical initiator is a peroxy compound or azo compound.

5. The process as claimed in claim 4, wherein the free-radical initiator and catalyst are used in a molar ratio of 4:1.

6. The process as claimed in claim 1, wherein the catalytic oxidation is carried out in the liquid phase at a temperature of 0 to 500° C.

7. The process as claimed in claim 1, wherein the oxidizing agent is a gas containing 5 to 100% by volume of oxygen.

8. The process as claimed in claim 1, wherein the catalytic oxidation is carried out under a pressure of 1 to 100 bar.

9. The process as claimed in claim 1, wherein the hydrocarbon to be oxidized contains oxygen, nitrogen and/or sulfur atoms and/or cyano groups.

10. The process as claimed in claim 1, wherein the substrate to be oxidized is a hydrocarbon of the formula IV

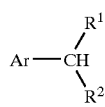   IV where

R$^1$, R$^2$=H, aliphatic or aromatic hydro-carbon radical having 1 to 20 carbon atoms, where R$^1$ and R$^2$ are identical or different radicals and R$^1$ and R$^2$ can be linked to one another via a covalent bond and Ar=aromatic hydrocarbon radical.

11. The process as claimed in claim 1, wherein the substrate to be oxidized is a hydrocarbon of the formulae V, VI, VII and VIII

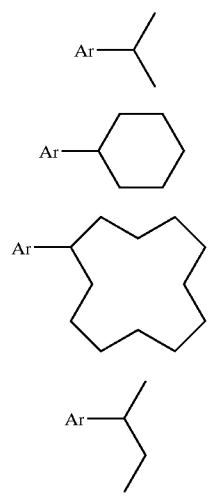

where Ar=aromatic hydrocarbon radical.

12. The process as claimed in claim 1, wherein the substrate to be oxidized is a cyclic, saturated, substituted or unsubstituted hydrocarbon of the formula X

   X where n=3 to 21.

13. The process as claimed in claim 1, wherein the substrate to be oxidized is aminocyclododecane, butadiene, butene, butyl-benzene, cumene, cyclodecadiene, cyclodecane, cyclodecene, cyclododecadiene, cyclododecane, cyclododecanol, cyclododecanone, cyclododecatriene, cyclododecene, cyclododecylbenzene, cyclohexane, cyclohexanol, cyclohexene, cyclohexanone, cycloheptene, cyclohexylbenzene, cyclononene, cyclooctanol, cyclooctane, cyclooctanol, cyclooctanone, cyclooctene, cyclopentadecane, cyclo-pentadecanol, cyclopentadecanone, cyclopentadecatriene, cyclopentadecene, cyclopentadecadiene, decalin, dicyclododecyl ether, ethylbenzene, isobutane, isobutene, isophorone, isophorone derivatives, meta-xylene, ortho-xylene, para-xylene, picoline, propane, propene, tetralin, toluene, trimethylcyclohexane, trimethylcyclo-hexanol, trimethylcyclohexanone, trivinylcyclo-hexane, in each case as pure substance, in solution or as a mixture.

14. The process as claimed in claim 1, wherein the substrate to be oxidized is a cyclic, saturated, substituted or unsubstituted hydrocarbon of the formula XI

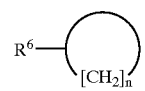   XI where R$^6$=OH or an alkyl chain having 1–10 carbon atoms and n=3–21.

15. The process as claimed in claim 1, wherein the substrate to be oxidized is a wax of natural or synthetic origin.

16. The process as claimed in claim 1, wherein the catalytic oxidation is carried out in the presence of ammonia.

17. The process as claimed in claim 1, wherein the molar ratio of the catalyst to the saturated or unsaturated substituted or unsubstituted hydrocarbon ranges from $10^{-6}$ mol % to 1 mol %.

18. The process as claimed in claim 1, wherein the molar ratio of the catalyst to the saturated or unsaturated substituted or unsubstituted hydrocarbon ranges from $10^{-6}$ mol % to 0.1 mol %.

19. The process as claimed in claim 1, wherein the saturated or unsaturated substituted or unsubstituted hydrocarbon is employed as a solvent.

* * * * *

UNITED STATES PATENT AND TRADEMARK OFFICE
CERTIFICATE OF CORRECTION

PATENT NO. : 6,852,893 B2
DATED : February 8, 2005
INVENTOR(S) : Kuehnle et al.

It is certified that error appears in the above-identified patent and that said Letters Patent is hereby corrected as shown below:

<u>Title page,</u>
Item [75], Inventors, should read:
-- [75] Inventors: Adolf Kühnle, Marl (DE); Mark Duda, Ludwigshafen (DE); Carsten Jost, Marl (DE); Guido Fries, Recklinghausen (DE); Jochen Kirchhoff, Luedinghausen (DE); Thomas Schiffer, Haltern (DE); Roger Arthur Sheldon, Rijswijk (NL); Sasidharan Manickam, Tamil Nadu (IN); Isabella W.C.E. Arends, Gravenhage (NL) --
Item [73], Assignee, should read :
-- [73] Assignee: Creavis Gesellschaft fuer Technologie und Innovation mbH, Marl (DE) --
Item [45] and [*] Notice, should read as follows:
-- [45] **Date of Patent: *Feb, 8, 2005**

[*] Notice: Subject to any disclaimer, the term of this patent is extend or adjusted under 35 U.S.C. 154(b) by 0 days.

This Patent is subject to a terminal disclaimer. --

Signed and Sealed this

Seventeenth Day of May, 2005

JON W. DUDAS
*Director of the United States Patent and Trademark Office*